US006482781B2

(12) United States Patent
Graham et al.

(10) Patent No.: US 6,482,781 B2
(45) **Date of Patent: *Nov. 19, 2002**

(54) MULTI-PURPOSE CONTACT LENS CARE COMPOSITIONS

(75) Inventors: Richard Graham, Irvine, CA (US); Joseph G. Vehige, Laguna Niguel, CA (US)

(73) Assignee: Advanced Medical Optics, Inc., Santa Ana, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/968,253

(22) Filed: Oct. 1, 2001

(65) Prior Publication Data

US 2002/0035045 A1 Mar. 21, 2002

Related U.S. Application Data

(63) Continuation of application No. 09/417,526, filed on Oct. 13, 1999, now Pat. No. 6,319,883, which is a continuation of application No. 08/980,033, filed on Nov. 26, 1997, now Pat. No. 6,063,745.

(51) Int. Cl.[7] .......................... C11D 1/722; C11D 3/06; C11D 3/48; A61K 31/155

(52) U.S. Cl. ...................... 510/112; 510/113; 510/421; 510/473; 510/480; 422/28; 424/78.04

(58) Field of Search ................................ 510/112, 113, 510/421, 473, 480; 422/28; 424/78.04

(56) References Cited

U.S. PATENT DOCUMENTS

| | | | | |
|---|---|---|---|---|
| 3,311,577 A | | 3/1967 | Rankin | |
| 4,029,817 A | | 6/1977 | Blanco et al. | |
| 4,046,706 A | | 9/1977 | Krezanoski | |
| 4,323,467 A | | 4/1982 | Fu | |
| 4,510,065 A | | 4/1985 | Sherman | |
| 4,525,346 A | | 6/1985 | Stark | |
| 4,551,461 A | | 11/1985 | Sherman | |
| 4,581,374 A | | 4/1986 | Nelson et al. | |
| 4,626,292 A | | 12/1986 | Sherman | |
| 4,758,595 A | | 7/1988 | Ogunbiyi | |
| 4,880,601 A | | 11/1989 | Andermann et al. | |
| 4,904,698 A | | 2/1990 | Adkins, Jr. et al. | |
| 5,300,296 A | | 4/1994 | Holly et al. | |
| 5,322,667 A | | 6/1994 | Sherman | |
| 5,401,327 A | | 3/1995 | Ellis et al. | |
| 5,405,878 A | * | 4/1995 | Ellis et al. | 422/28 |
| 5,422,029 A | | 6/1995 | Potini et al. | |
| 5,453,435 A | | 9/1995 | Rahejha et al. | |
| 5,494,937 A | | 2/1996 | Asgharian et al. | |
| 5,500,141 A | | 3/1996 | Potini et al. | |
| 5,500,144 A | | 3/1996 | Potini et al. | |
| 5,532,224 A | | 7/1996 | Desai et al. | |
| 5,580,392 A | | 12/1996 | Sulc et al. | |
| 5,589,387 A | | 12/1996 | Cafaro | |
| 5,591,426 A | | 1/1997 | Dabrowski et al. | |
| 5,607,908 A | | 3/1997 | Potini et al. | |
| 5,653,972 A | | 8/1997 | Desai et al. | |
| 5,719,110 A | | 2/1998 | Cook | |
| 5,765,579 A | | 6/1998 | Heiler et al. | |
| 5,773,396 A | | 6/1998 | Zhang et al. | |
| 6,063,745 A | | 5/2000 | Graham et al. | |
| 6,319,883 B1 | * | 11/2001 | Graham et al. | 510/112 |

FOREIGN PATENT DOCUMENTS

| | | |
|---|---|---|
| GB | 1432345 | 4/1972 |
| GB | 1437345 | 4/1976 |
| WO | 9832421 | 7/1998 |

* cited by examiner

*Primary Examiner*—Lorna M. Douyon
(74) *Attorney, Agent, or Firm*—Stout, Uxa, Buyan & Mullins, LLP; Frank J. Uxa; Peter Jon Gluck

(57) ABSTRACT

Multi-purpose solutions for contact lens care provide substantial lens wearer/user comfort and/or acceptability. Such solutions include an aqueous liquid medium; an antimicrobial component, preferably a biguanide polymer present in an amount of less than about 5 ppm; a surfactant component, preferably a poly(oxyethylene)-poly(oxypropylene) block copolymer surfactant, in an effective amount; a phosphate buffer component in an effective amount; a viscosity inducing component, preferably selected from cellulosic derivatives, in an effective amount; and a tonicity component in an effective amount. Such solutions have substantial performance, comfort and-acceptability benefits, which, ultimately, lead to ocular health advantages and avoidance of problems caused by contact lens wear.

11 Claims, No Drawings

MULTI-PURPOSE CONTACT LENS CARE COMPOSITIONS

This application is a continuation of application Ser. No.: 09/417,526, filed Oct. 13, 1999 now U.S. Pat. No. 6,319,883 which, in turn, is a continuation of application Ser. No. 08/980,033 filed Nov. 26, 1997 now U.S. Pat. No. 6,063,745.

BACKGROUND OF THE INVENTION

The present invention relates to compositions for treating, for example, disinfecting, cleaning, soaking, conditioning and wetting contact lenses. More particularly, the invention relates to multi-purpose solutions useful in treating contact lenses, for example, for disinfecting contact lenses, for removing deposit material from contact lenses, for soaking, conditioning and/or wetting contact lenses and the like, which provide substantial comfort and acceptability benefits to the users of such solutions.

Contact lenses need to be periodically treated, for example, disinfected, cleaned, soaked and the like, on a regular basis because of the tendency for a variety of ocular and environmental contaminants, microbes and other materials to accumulate on the lenses and/or the need to provide the lenses in suitable condition for safe and comfortable wear. User compliance, that is users treating contact lenses on a regular and consistent basis, is important in order to promote ocular health and to avoid problems associated with contact lens wear. User compliance is enhanced when the treatment solution employed provides high degrees of lens wearer/user comfort and acceptability. Therefore, it would be advantageous to provide compositions for treating contact lenses which provide such comfort and/or are accepted by contact lens wearers/users of such compositions.

Fu U.S. Pat. No. 4,323,467 discloses an aqueous composition combining a poly(oxyethylene)-poly(oxypropylene) substituted ethylenediamine surfactant, a germicidal agent, a viscosity builder, a tonicity agent, a sequestering agent and water for treating rigid contact lenses. This patent discloses a germicide, such as thimerosal and/or benzalkonium chloride, in a concentration of 0.0005%–0.05%. The Fu patent does not disclose the use of any specific buffer. Although the compositions of the Fu patent have multiple utilities, there is a potential for eye discomfort and/or irritation, for example, because of the relatively high concentrations of germicide and the apparent lack of pH control.

British Patent 1,432,345 discloses a contact lens disinfecting composition including an ophthalmically acceptable biguanide in a total amount of from 0.0005% to 0.05% by weight. This British patent discloses that the solution preferably has a pH of from 5 to 8 and employs a phosphate buffer. The patent also discloses employing additional bactericides, thickening agents and non-ionic surfactants, as well as disodium EDTA in concentrations of at least 0.1%. Although these compositions are effective as contact lens disinfectants, they do pose a risk of eye discomfort and/or irritation, for example, because of the relatively high concentrations of biguanide and EDTA employed.

Ogunbiyi et al U.S. Pat. No. 4,758,595 discloses an aqueous solution of a biguanide in an amount of 0.000001 to 0.0003% weight percent in combination with a borate buffer system, EDTA, and one or more surfactants. This U.S. patent additionally states that conventional buffers, other than the borate buffer, can be used but only in conjunction with increased amounts of biguanide. Thus, the general conclusion of this U.S. Patent is that if reduced amounts of biguanide are to be used, a borate buffer is essential. Although such compositions are useful, the potential for ocular discomfort and irritation in a relatively large percentage of the total population still exists, for example, because of the requirement that a borate buffer be employed.

There continues to be a need to provide new contact lens treatment systems, for example, multi-purpose solutions, that effect the desired treatment or treatments of the lens and, at the same time, provide substantial, preferably enhanced, lens wearer/user comfort and acceptability.

SUMMARY OF THE INVENTION

New compositions for treating contact lenses have been discovered. The present compositions, that is multi-purpose aqueous solutions, include antimicrobial components, preferably reduced concentrations of antimicrobial components, in combination with phosphate buffers and viscosity inducing components to provide the desired antimicrobial activity and performance effectiveness and, importantly, substantial, preferably enhanced, lens wearer/user comfort and acceptability benefits. These compositions are surprising and unexpected in view of the above-noted prior art which employs relatively large concentrations of antimicrobial components and/or buffering systems other than phosphate buffering systems and/or does not employ viscosity inducing components. In addition, the inclusion of one or more other components in the present compositions is effective in providing additional beneficial properties to the compositions, and preferably provide further lens wearer/user comfort and acceptability benefits. The present compositions have a multitude of applications, for example, as disinfecting, cleaning, soaking, wetting and conditioning compositions, for contact lens care, while providing substantial lens wearer/user comfort and acceptability. The present compositions preferably increase user compliance, that is promote regular and consistent contact lens care, and, ultimately, lead to or facilitate better ocular health.

In one embodiment of the present invention, multi-purpose solutions for contact lens care are provided. Such solutions comprise an aqueous liquid medium; an antimicrobial component in an amount effective to disinfect a contact lens contacted with the solution; a surfactant in an amount effective in cleaning a contact lens contacted with the solution; a phosphate buffer component in an amount effective in maintaining the pH of the solution within a physiologically acceptable range; a viscosity inducing component present in an effective amount; and a tonicity component in an amount effective in providing the desired tonicity to the solution.

The antimicrobial component may be any suitable, preferably ophthalmically acceptable, material effective to disinfect a contact lens contacted with the present solutions. Preferably, the antimicrobial component is selected from biguanides, biguanides polymers, salts thereof and mixtures thereof, and is present in an amount in the range of about 0.1 ppm to about 3 ppm or less than 5 ppm (w/v). The preferred relatively reduced concentration of the antimicrobial component has been found to be very effective, in the present compositions, in disinfecting contact lenses contacted with the compositions, while at the same time promoting lens wearer/user comfort and acceptability.

Any suitable, preferably ophthalmically acceptable, surfactant component which is effective in cleaning contact lenses may be employed. The surfactant component preferably is non-ionic and, more preferably, is selected from poly(oxyethylene)-poly(oxypropylene) block copolymers and mixtures thereof.

Any suitable, preferably ophthalmically acceptable, viscosity inducing or thickening agent may be included in the present compositions. The viscosity inducing component preferably is selected from cellulosic derivatives and mixtures thereof and is present in an amount in the range of about 0.05% to about 0.5% (w/v). Without wishing to limit the invention to any particular theory of operation, it is believed that the presence of a viscosity inducing component at least assists in providing the lens wearer/user comfort and acceptability benefits of the present invention, which promote regular and consistent contact lens care and ultimately lead to or facilitate better ocular health. The present combinations of components, for example, including such viscosity inducing components, are effective in providing the degree of lens wearer/user comfort and acceptability benefits described herein.

Although any suitable, preferably ophthalmically acceptable, tonicity component may be employed, a very useful tonicity component is a combination of sodium chloride and potassium chloride.

The present compositions preferably include an effective amount of a chelating component. Any suitable, preferably ophthalmically acceptable, chelating component may be included in the present compositions, although ethylenediaminetetraacetic acid (EDTA), salts thereof and mixtures thereof are particularly effective. More preferably, the present compositions include chelating components in effective amounts less than about 0.05% (w/v) and still more preferably 0.02% (w/v) or less. Such reduced amounts of chelating component in the present compositions remain effective in providing the desired chelating and/or sequestering functions while, at the same time, are better tolerated in the eye, thereby reducing the risk of user discomfort and/or ocular irritation.

Various combinations of two or more of the above-noted components may be used in providing at least one of the benefits described herein. Therefore, each and every such combination is included within the scope of the present invention.

These and other aspects of the present invention are apparent in the following detailed description, examples and claims.

DETAILED DESCRIPTION OF THE INVENTION

The present invention is directed to multi-purpose solutions useful for treating, for example, disinfecting, cleaning, soaking, rinsing, wetting, conditioning and the like, contact lenses. Any contact lenses, for example, conventional hard contact lenses, rigid gas permeable contact lenses and soft, hydrophilic or hydrogel, contact lenses, can be treated in accordance with the present invention.

In one embodiment, the present compositions comprise a liquid aqueous medium; an antimicrobial component in the liquid aqueous medium in an amount effective to disinfect a contact lens contacted with the composition; a surfactant, preferably a non-ionic surfactant, component in an amount effective in cleaning a contact lens contacted with the composition; a phosphate buffer component in an amount effective in maintaining the pH of the composition within a physiologically acceptable range; an effective amount of a viscosity inducing component; and an effective amount of a tonicity component. The present compositions preferably include an effective amount of a chelating or sequestering component, more preferably in a range of less than 0.05% (w/v). Each of the components, in the concentration employed, included in the solutions and the formulated solutions of the present invention preferably are ophthalmically acceptable. In addition, each of the components, in the concentration employed, included in the present solutions preferably is soluble in the liquid aqueous medium.

A solution or component thereof is "ophthalmically acceptable" when it is compatible with ocular tissue, that is, it does not cause significant or undue detrimental effects when brought into contact with ocular tissue. Preferably, each component of the present compositions is also compatible with the other components of the present compositions. The present compositions are more preferably substantially ophthalmically optimized. An ophthalmically optimized composition is one which, within the constraints of component chemistry, minimizes ocular response, or conversely delivers ophthalmic benefit to the lens wearing eye.

The presently useful antimicrobial components include chemicals which derive their antimicrobial activity through a chemical or physiochemical interaction with microbes or microorganisms, such as those contaminating a contact lens. Suitable antimicrobial components are those generally employed in ophthalmic applications and include, but are not limited to, quaternary ammonium salts used in ophthalmic applications such as poly[dimethylimino-2-butene-1,4-diyl] chloride, alpha-[4-tris(2-hydroxyethyl) ammonium]-dichloride (chemical registry number 75345-27-6, available under the trademark Polyquaternium 1® from Onyx Corporation), benzalkonium halides, and biguanides, such as salts of alexidine, alexidine-free base, salts of chlorhexidine, hexamethylene biguanides and their polymers, and salts thereof, antimicrobial polypeptides, chlorine dioxide precursors, and the like and mixtures thereof. Generally, the hexamethylene biguanide polymers (PHMB), also referred to as polyaminopropyl biguanide (PAPB), have molecular weights of up to about 100,000. Such compounds are known and are disclosed in Ogunbiyi et al U.S. Pat. No. 4,758,595, the disclosure of which is hereby incorporated in its entirety by reference herein.

The antimicrobial components useful in the present invention preferably are present in the liquid aqueous medium in concentrations in the range of about 0.00001% to about 2% (w/v).

More preferably, the antimicrobial component is present in the liquid aqueous medium at an ophthalmically acceptable or safe concentration such that the user can remove the disinfected lens from the liquid aqueous medium and thereafter directly place the lens in the eye of safe and comfortable wear.

The antimicrobial components suitable for inclusion in the present invention include chlorine dioxide precursors. Specific examples of chlorine dioxide precursors include stabilized chlorine dioxide (SCD), metal chlorites, such as alkali metal and alkaline earth metal chlorites, and the like and mixtures thereof. Technical grade sodium chlorite is a very useful chlorine dioxide precursor. Chlorine dioxide-containing complexes such as complexes of chlorine dioxide with carbonate, chlorine dioxide with bicarbonate and mixtures thereof are also included as chlorine dioxide precursors. The exact chemical composition of many chlorine dioxide precursors, for example, SCD and the chlorine dioxide complexes, is not completely understood. The manufacture or production of certain chlorine dioxide precursors is described in McNicholas U.S. Pat. No. 3,278,447, which is incorporated in its entirety herein by reference. Specific examples of useful SCD products include that sold under the trademark Dura Klor by Rio Linda Chemical Company, Inc., and that sold under the trademark Anthium Dioxide by International Dioxide, Inc.

If a chlorine dioxide precursor in included in the present compositions, it preferably is present in an effective contact lens disinfecting amount. Such effective disinfecting concentrations preferably are in the range of about 0.002 to about 0.06% (w/v) of the present compositions. Such chlorine dioxide precursors may be used in combination with other antimicrobial components, such as biguanides, biguanide polymers, salts thereof and mixtures thereof.

In the event that chlorine dioxide precursors are employed as antimicrobial components, the compositions preferably have an osmolality of at least about 200 mOsmol/kg and are buffered to maintain the pH within an acceptable physiological range, for example, a range of about 6 to about 10.

In one embodiment, the antimicrobial component is non-oxidative. It has been found that reduced amounts of non-oxidative antimicrobial components, for example, in a range of about 0.1 ppm to about 3 ppm or less than 5 ppm (w/v), in the present compositions are effective in disinfecting contact lenses and reduce the risk of such antimicrobial components causing ocular discomfort and/or irritation. Such reduced concentration of antimicrobial component is very useful when the antimicrobial component employed is selected from biguanides, biguanide polymers, salts thereof and mixtures thereof.

When a contact lens is desired to be disinfected by the present compositions, an amount of the antimicrobial component effective to disinfect the lens is used. Preferably, such an effective amount of the antimicrobial component reduces the microbial burden or load on the contact lens by one log order in three hours. More preferably, an effective amount of the disinfectant reduces the microbial load by one log order in one hour.

The phosphate buffer component is present in an amount effective to maintain the pH of the composition or solution in the desired range, for example, in a physiologically acceptable range of about 4 or about 5 or about 6 to about 8 or about 9 or about 10. In particular, the solution preferably has a pH in the range of about 6 to about 8. The phosphate buffer component preferably includes one or more phosphate buffers, for example, combinations of monobasic phosphates, dibasic phosphates and the like. Particularly useful phosphate buffers are those selected from phosphate salts of alkali and/or alkaline earth metals. Examples of suitable phosphate buffers include one or more of sodium dibasic phosphate ($Na_2HPO_4$), sodium monobasic phosphate ($NaH_2PO_4$) and potassium monobasic phosphate ($KH_2PO_4$). The present buffer components frequently are used in amounts in a range of about 0.01% or about 0.02% to about 0.5% (w/v), calculated as phosphate ion.

The present compositions preferably further comprise effective amounts of one or more additional components, such as a detergent or surfactant component; a viscosity inducing or thickening component; a chelating or sequestering component; a tonicity component; and the like and mixtures thereof. The additional component or components may be selected from materials which are known to be useful in contact lens care compositions and are included in amounts effective to provide the desired effect or benefit. When an additional component is included, it is preferably compatible under typical use and storage conditions with the other components of the composition. For instance, the aforesaid additional component or components preferably are substantially stable in the presence of the antimicrobial and buffer components described herein.

A surfactant component preferably is present in an amount effective in cleaning, that is to at least facilitate removing, and preferably effective to remove, debris or deposit material from, a contact lens contacted with the surfactant-containing solution. Exemplary surfactant components include, but are not limited to, nonionic surfactants, for example, polysorbates (such as polysorbate 20-Trademark Tween 20), 4-(1,1,3,3-tetramethylbutyl) phenol/poly(oxyethylene) polymers (such as the polymer sold under the trademark Tyloxapol), poly(oxyethylene)-poly(oxypropylene) block copolymers, glycolic esters of fatty acids and the like, and mixtures thereof.

The surfactant component preferably is nonionic, and more preferably is selected from poly(oxyethylene)-poly(oxypropylene) block copolymers and mixtures thereof. Such surfactant components can be obtained commercially from the BASF Corporation under the trademark Pluronic®. Such block copolymers can be generally described as polyoxyethylene/polyoxypropylene condensation polymers terminated in primary hydroxyl groups. They may be synthesized by first creating a hydrophobe of desired molecular weight by the controlled addition of propylene oxide to the two hydroxyl groups of propylene glycol. In the second step of the synthesis, ethylene oxide is added to sandwich this hydrophobe between hydrophile groups.

In accordance with a more preferred embodiment of the invention, such block copolymers having molecular weights in the range of about 2500 to 13,000 daltons are suitable, with a molecular weight range of about 6000 to about 12,000 daltons being still more preferred. Specific examples of surfactants which are satisfactory include: poloxamer 108, poloxamer 188, poloxamer 237, poloxamer 238, poloxamer 288 and poloxamer 407. Particularly good results are obtained poloxamer 237.

The amount of surfactant component, if any, present varies over a wide range depending on a number of factors, for example, the specific surfactant or surfactants being used, the other components in the composition and the like. Often the amount of surfactant is in the range of about 0.005% or about 0.01% to about 0.1% or about 0.5% or about 0.8% (w/v).

The viscosity inducing components employed in the present solutions preferably are effective at low or reduced concentrations, are compatible with the other components of the present solutions and are nonionic. Such viscosity inducing components are effective to enhance and/or prolong the cleaning and wetting activity of the surfactant component and/or condition the lens surface rendering it more hydrophilic (less lipophilic) and/or to act as a demulcent on the eye. Increasing the solution viscosity provides a film on the lens which may facilitate comfortable wearing of the treated contact lens. The viscosity inducing component may also act to cushion the impact on the eye surface during insertion and serves also to alleviate eye irritation.

Suitable viscosity inducing components include, but are not limited to, water soluble natural gums, cellulose-derived polymers and the like. Useful natural gums include guar gum, gum tragacanth and the like. Useful cellulose-derived viscosity inducing components include cellulose-derived polymers, such as hydroxypropyl cellulose, hydroxypropylmethyl cellulose, carboxymethyl cellulose, methyl cellulose, hydroxyethyl cellulose and the like. More preferably, the viscosity inducing agent is selected from cellulose derivatives (polymers) and mixtures thereof.

A very useful viscosity inducing component is hydroxypropylmethyl cellulose (HPMC).

The viscosity inducing component is used in an amount effective to increase the viscosity of the solution, preferably to a viscosity in the range of about 1.5 to about 30, or even as high as about 750, cps at 25° C., preferably as determined by USP test method No. 911 (USP 23, 1995). To achieve this range of viscosity increase, an amount of viscosity inducing component of about 0.01% to about 5% (w/v) preferably is employed, with amounts of about 0.05% to about 0.5% being more preferred.

A chelating or sequestering component preferably is included in an amount effective to enhance the effectiveness of the antimicrobial component and/or to complex with metal ions to provide more effective cleaning of the contact lens.

A wide range of organic acids, amines or compounds which include an acid group and an amine function are capable of acting as chelating components in the present compositions. For example, nitrilotriacetic acid, diethylenetriaminepentacetic acid, hydroxyethylethylenediaminetriacetic acid, 1,2-diaminocyclohexane tetraacetic acid, hydroxyethylaminodiacetic acid, ethylenediaminetetraacetic acid and its salts, polyphosphates, citric acid and its salts, tartaric acid and its salts, and the like and mixtures thereof, are useful as chelating components. Ethylenediaminetetraacetic acid (EDTA) and its alkali metal salts, are preferred, with disodium salt of EDTA, also known as disodium edetate, being particularly preferred.

The chelating component preferably is present in an effective amount, for example, in a range of about 0.01% and about 1% (w/v) of the solution.

In a very useful embodiment, particularly when the chelating component is EDTA, salts thereof and mixtures thereof, a reduced amount is employed, for example, in the range of less than about 0.05% (w/v) or even about 0.02% (w/v) or less. Such reduced amounts of chelating component have been found to be effective in the present compositions while, at the same time, providing for reduced discomfort and/or ocular irritation.

The liquid aqueous medium used is selected to have no substantial deleterious effect on the lens being treated, or on the wearer of the treated lens. The liquid medium is constituted to permit, and even facilitate, the lens treatment or treatments by the present compositions. The liquid aqueous medium advantageously has an osmolality in the range of at least about 200 mOsmol/kg for example, about 300 or about 350 to about 400 mOsmol/kg. The liquid aqueous medium more preferably is substantially isotonic or hypertonic (for example, slightly hypertonic) and/or is ophthalmically acceptable.

The liquid aqueous medium preferably includes an effective amount of a tonicity component to provide the liquid medium with the desired tonicity. Such tonicity components may be present in the liquid aqueous medium and/or may be introduced into the liquid aqueous medium. Among the suitable tonicity adjusting components that may be employed are those conventionally used in contact lens care products, such as various inorganic salts. Sodium chloride and/or potassium chloride and the like are very useful tonicity components. The amount of tonicity component included is effective to provide the desired degree of tonicity to the solution. Such amount may, for example, be in the range of about 0.4% to about 1.5% (w/v). If a combination of sodium chloride and potassium chloride is employed, it is preferred that the weight ratio of sodium chloride to potassium chloride be in the range of about 3 to about 6 or about 8.

Methods for treating a contact lens using the herein described compositions are included within the scope of the invention. Such methods comprise contacting a contact lens with such a composition at conditions effective to provide the desired treatment to the contact lens.

The contacting temperature is preferred to be in the range of about 0° C. to about 100° C., and more preferably in the range of about 10° C. to about 60° C. and still more preferably in the range of about 15° C. to about 30° C. Contacting at or about ambient temperature is very convenient and useful. The contacting preferably occurs at or about atmospheric pressure. The contacting preferably occurs for a time in the range of about 5 minutes or about 1 hour to about 12 hours or more.

The contact lens can be contacted with the liquid aqueous medium by immersing the lens in the medium. During at least a portion of the contacting, the liquid medium containing the contact lens can be agitated, for example, by shaking the container containing the liquid aqueous medium and contact lens, to at least facilitate removal of deposit material from the lens. After such contacting step, the contact lens may be manually rubbed to remove further deposit material from the lens. The cleaning method can also include rinsing the lens substantially free of the liquid aqueous medium prior to returning the lens to a wearer's eye.

The following non-limiting examples illustrate certain aspects of the present invention.

EXAMPLE 1

A solution is prepared by blending together the following components:

| Component | Amount |
|---|---|
| PHMB (polyhexamethylene biguanide) | 1 ppm (w/v) |
| Disodium EDTA | 0.02% (w/v) |
| Poloxamer 237 (poly(oxyethylene)-poly (oxypropylene) block copolymer) | 0.05% (w/v) |
| Sodium Phosphate Dibasic (heptahydrate) | 0.12% (w/v) |
| Sodium Phosphate Monobasic (monohydrate) | 0.01% (w/v) |
| HPMC (Hydroxypropylmethyl Cellulose) | 0.15% (w/v) |
| Sodium Chloride | 0.79% (w/v) |
| Potassium Chloride | 0.14% (w/v) |
| Water (USP) | Q.S. 100% |

Approximately three (3) ml of this solution is introduced into a lens vial containing a lipid, oily deposit laden, hydrophilic or soft contact lens. The contact lens is maintained in this solution at room temperature for at least about four (4) hours. This treatment is effective to disinfect the contact lens. In addition, it is found that a substantial portion of the deposits previously present on the lens has been removed. This demonstrates that this solution has substantial passive contact lens cleaning ability. Passive cleaning refers to the cleaning which occurs during soaking of a contact lens, without mechanical or enzymatic enhancement.

After this time, the lens is removed from the solution and is placed in the lens wearer's eye for safe and comfortable wear. Alternately, after the lens is removed from the solution, it is rinsed with another quantity of this solution and the rinsed lens is then placed in the lens wearer's eye for safe and comfortable wear.

EXAMPLE 2

Example 1 is repeated except that the lens is rubbed and rinsed with a different quantity of the solution prior to being placed in the lens vial. After at least about four (4) hours, the lens is removed from the solution. The lens is then placed in the lens wearer's eye for safe and comfortable wear.

EXAMPLE 3

The solution of Example 1 is used as a long-term soaking medium for a hydrophilic contact lens. Thus, approximately three (3) ml of this solution is placed in a vial and a contact lens is maintained in the solution at room temperature for about sixty (60) hours. After this soaking period, the lens is removed from the solution and placed in the lens wearer's eye for safe and comfortable wear. Alternately, after the lens is removed from the solution, it is rinsed with another quantity of this solution and the rinsed lens is then placed in the lens wearer's eye for safe and comfortable wear.

EXAMPLE 4

A hydrophilic contact lens is ready for wear. In order to facilitate such wearing, one or two drops of the solution of Example 1 is placed on the lens immediately prior to placing the lens in the lens wearer's eye. The wearing of this lens is comfortable and safe.

EXAMPLE 5

A lens wearer wearing a contact lens applies one or two drops of the solution of Example 1 in the eye wearing the lens. This effects a re-wetting of the lens and provides for comfortable and safe lens wear.

EXAMPLE 6

A series of tests are conducted to evaluate the comfort, safety and acceptability of the solution prepared in accordance with Example 1 compared to two other solutions.

The first of these other solutions, referred to hereinafter as Composition A, is sold under the trademark ReNu® by Bausch & Lomb and includes 0.5 ppm PHMB, a poly (oxyethylene)-poly(oxypropylene) substituted ethylenediamine surfactant, a borate buffer system, 0.1% disodium EDTA, and sodium chloride as a tonicity agent.

The second of these other solutions, referred to hereinafter as Composition B, is similar to the composition of Example 1 except that Composition B included 0.6% (w/v) tromethamine, and neither of the phosphates.

Each of these compositions is tested to evaluate its comfort, safety and acceptability for the care of hydrogel (hydrophilic) contact lenses worn on a daily basis among subjects previously adapted to at least one commercially available multi-purpose solution.

The study is a randomized, double-masked, three-way cross over study. The study is broken down into a series of three (3) one (1) month treatment periods. Each of the compositions is used on a daily basis for cleaning, rinsing after cleaning, disinfection, and rinsing prior to lens application, as needed. Because each treatment period is only one (1) month in duration, no enzymatic cleaner is used in this study.

The subjects are evaluated at day zero (baseline), day seven (7) and day thirty (30) for each of the three (3) treatment periods. The primary comfort and acceptability variables are lens wearing comfort and end of study product preference. The primary safety variable is slit lamp examination findings.

123 subjects are enrolled. 116 (94.3%) complete Preference Questionnaires for Treatment Period 2. 118 (95.9%) complete Preference Questionnaires for Treatment Period 3.

The results of this study are summarized as follows. The slit lamp examinations indicate that each of the compositions tested is acceptably safe. The comfort and acceptability results included in this summary are based on subjective answers to selected questions (at the end of Treatment Periods 2 and 3).

Further tabulations are made based on subjective answers to the selected questions noted above, as well as to other questions included in the Preference Questionnaires. These tabulations are made using answers from the Preference Questionnaires for Treatment Period 3.

Results of these further tabulations are as follows:

| Preference Question | Respondents Preferring Example 1 Composition % | Respondents Preferring Composition A % | No Preference | P Value |
|---|---|---|---|---|
| Overall preference | 65 | 28 | 7 | 0.02 |
| In-the-hand preference | 56 | 27 | 17 | 0.02 |
| In-the-eye preference | 63 | 27 | 11 | 0.02 |
| Comfort in-the-eye | 60 | 25 | 15 | 0.02 |
| Amount of time for lenses to settle in the eye | 47 | 21 | 32 | 0.02 |
| Keeping lenses moist in eyes | 55 | 28 | 17 | 0.02 |
| Keeping lenses lubricated in eyes | 57 | 28 | 15 | 0.02 |
| Soothing in eyes | 57 | 27 | 16 | 0.02 |

*BASED ON A P-VALUE OF 0.02, THESE RESULTS ARE SIGNIFICANT AT A 95% LEVEL OF CONFIDENCE

| Preference Question | Respondents Preferring Composition B Composition % | Respondents Preferring Composition A % | No Preference | P Value |
|---|---|---|---|---|
| Overall preference | 55 | 40 | 5 | 0.18 |
| In-the-hand preference | 51 | 31 | 18 | 0.08 |
| In-the-eye preference | 60 | 34 | 6 | 0.02 |
| Comfort in-the-eye | 36 | 34 | 10 | 0.06 |
| Amount of time for lenses to settle in the eye | 44 | 31 | 25 | 0.26 |
| Keeping lenses moist in eyes | 47 | 34 | 19 | 0.26 |
| Keeping lenses lubricated in eyes | 47 | 32 | 21 | 0.18 |
| Soothing in eyes | 57 | 32 | 10 | 0.02 |

These results indicate a clear preference of the composition of Example 1 over Composition A; and an overall preference of the composition of Example 1 over Composition B.

These results are indeed surprising since Composition A is a commercially available multi-purpose solution. Possible reasons for the preference of the Example 1 composition relative to Composition A include one or more of the presence of HPMC, the presence of a poly(oxyethylene)-poly(oxypropylene) block copolymer surfactant, the presence of the phosphate buffer, and/or the presence of a reduced amount of EDTA.

The present compositions provide a very beneficial and advantageous combination of performance efficacy and lens wearer/user comfort and acceptability. In the context of contact lens care solutions, lens wearer/user comfort and acceptability are very important, for example, to promote regular and effective treating of contact lenses. Such treating of contact lenses ultimately promotes ocular health and reduces the frequency of problems caused by wearing contact lenses. Thus, lens wearer/user comfort and acceptability are of substantial importance and benefit in a contact lens care product, in particular in the present compositions which exhibit substantial, even enhanced, lens wearer/user comfort and acceptability.

While this invention has been described with respect to various specific examples and embodiments, it is to be understood that the invention is not limited thereto and that it can be variously practiced within the scope of the following claims.

What is claimed is:

1. A multi-purpose solution for contact lens care comprising:

an aqueous liquid medium;

polyhexamethylene biguanide present in an amount in a range of about 0.1 ppm to less tha 5 ppm;

a poly (oxyethylene)-poly (oxypropylene) block copolymer surfactant in an amount effective in cleaning a contact lens contacted with said solution;

a phosphate buffer component in an amount effective in maintaining the pH of said solution within a physiologically acceptable range;

hydroxypropylmethylcellulose in an amount effective in increasing the viscosity of said solution;

an effective amount of a chelating component selected from the group consisting of ethylenediaminetetraacetic acid, alkali metal salts of ethylenediaminetetraacetic acid and mixtures thereof in a range of less than 0.05% (w/v); and a tonicity component, including chloride, in an amount effective in providing the desired tonicity to said solution, said solution being preferred for overall performance relative to another multi-purpose solution containing an aqueous liquid medium, 0.5 ppm polyhexamethylene biguanide, a poly(oxyethylene)-poly (oxypropylene) substituted ethylenediamine surfactant, a borate buffer system, 0.1% w/v disodium EDTA and a sodium chloride tonicity agent in a randomized, double masked, three-way crossover study.

2. The multi-purpose solution of claim 1 wherein said surfactant is present in an amount in the range of about 0.01% to about 0.8% (w/v).

3. The multi-purpose solution of claim 1 wherein said phosphate buffer component includes a combination of sodium hydrogen phosphate and sodium dihydrogen phosphate.

4. The multi-purpose solution of claim 1 wherein said phosphate buffer component is present in an amount in a range of about 0.01% to about 0.5% (w/v).

5. The multi-purpose solution of claim 1 wherein said tonicity component includes a combination of sodium chloride and potassium chloride and is present in a range of about 0.4% to about 1.5% (w/v).

6. A multi-purpose solution for contact lens care comprising:

an aqueous liquid medium;

polyhexamethylene biguanide present in an amount in a range of about 0.1 ppm to less than 5 ppm;

a poly(oxyethylene)-poly(oxypropylene) block copolymer surfactant in an amount effective in cleaning a contact lens contacted with said solution;

a phosphate buffer component in an amount effective in maintaining the pH of said solution within an physiologically acceptable range;

a viscosity inducing component selected from the group consisting of cellulosic derivatives and mixtures thereof and being present in an effective amount in a range of about 0.05% to about 0.5% (w/v);

a chelating component selected from the group consisting of ethylenediaminetetraacetic acid, alkali metal salts of ethylenediaminetetraacetic acid and mixtures thereof in an effective amount of less than 0.05% (w/v);

a tonicity component, including chloride, in an amount effective in providing the desired tonicity to said solution, said solution being preferred for overall performance relative to another multi-purpose solution containing an aqueous liquid medium, 0.5 ppm polyhexamethylene biguanide, a poly(oxyethylene)-poly (oxypropylene) substituted ethylenediamine surfactant, a borate buffer system, 0.1% w/v disodium EDTA and a sodium chloride tonicity agent in a randomized, double-masked, three-way crossover study.

7. The multi-purpose solution of claim 6 wherein said surfactant is present in an amount in the range of about 0.01% to about 0.8% (w/v).

8. The multi-purpose solution of claim 6 wherein said phosphate buffer component includes a combination of sodium hydrogen phosphate and sodium dihydrogen phosphate.

9. The multi-purpose solution of claim 6 wherein said phosphate buffer component is present in an amount in a range of about 0.01% to about 0.5% (w/v).

10. The multi-purpose solution of claim 6 wherein said tonicity component includes a combination of sodium chloride and potassium chloride and is present in a range of about 0.4% to about 1.5%.

11. The multi-purpose solution of claim 6 wherein the viscosity including component is hydroxypropylmethylcellulose.

* * * * *

UNITED STATES PATENT AND TRADEMARK OFFICE

CERTIFICATE OF CORRECTION

PATENT NO. : 6,482,781 B2
DATED : November 19, 2002
INVENTOR(S) : Graham et al.

It is certified that error appears in the above-identified patent and that said Letters Patent is hereby corrected as shown below:

Title page,
Item [57], ABSTRACT,
Line 12, "and-acceptability benefits" should read -- and acceptability benefits --

Column 11,
Line 25, "less tha 5 ppm" should read -- less than 5 ppm --.

Signed and Sealed this

Tenth Day of June, 2003

JAMES E. ROGAN
*Director of the United States Patent and Trademark Office*